US012788258B2

(12) United States Patent
Xiang et al.

(10) Patent No.: US 12,788,258 B2
(45) Date of Patent: Nov. 10, 2026

(54) SYSTEM AND METHOD OF DUAL-MODE EAT/US-GUIDED ELECTROPORATION

(71) Applicant: THE REGENTS OF THE UNIVERSITY OF CALIFORNIA, Oakland, CA (US)

(72) Inventors: Liangzhong Xiang, Oakland, CA (US); Yifei Xu, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/869,803

(22) PCT Filed: May 30, 2023

(86) PCT No.: PCT/US2023/023896

§ 371 (c)(1),
(2) Date: Nov. 26, 2024

(87) PCT Pub. No.: WO2023/235332

PCT Pub. Date: Dec. 7, 2023

(65) Prior Publication Data

US 2025/0311929 A1 Oct. 9, 2025

Related U.S. Application Data

(60) Provisional application No. 63/347,493, filed on May 31, 2022.

(51) Int. Cl.
*A61B 5/00* (2006.01)
*G01S 7/52* (2006.01)

(52) U.S. Cl.
CPC ........ *A61B 5/0093* (2013.01); *G01S 7/52057* (2013.01); *A61B 2576/00* (2013.01)

(58) Field of Classification Search
CPC .............. A61B 5/0093; A61B 2576/00; A61B 2018/00613; A61B 8/5207; A61B 8/54; A61B 8/15
See application file for complete search history.

(56) References Cited

U.S. PATENT DOCUMENTS 12,036,405 B2 * 7/2024 Zarafshani ........... A61N 1/3603
2010/0049044 A1 2/2010 Burcher
(Continued)

FOREIGN PATENT DOCUMENTS

WO WO-2022/081763 A1 4/2022

OTHER PUBLICATIONS

Xu et al., "Electroacoustic tomography for real-time visualization of electrical field dynamics in deep tissue during electroporation"; 2023, Communications Engineering, Oct. 2023, vol. 2 (1), p. 75-9, Article 75 (Year: 2023).*
(Continued)

*Primary Examiner* — Baisakhi Roy
(74) *Attorney, Agent, or Firm* — FOLEY & LARDNER LLP

(57) ABSTRACT

The present embodiments relate generally to medical care and more particularly to a new imaging modality referred to herein as electroacoustic tomography (EAT) that not only depicts electrical field energy distribution in real time, but also enables clear discrimination between IRE and RE zones in situ during the treatment. According to some aspects, EAT exploits the phenomenon that the amplitude of acoustic emission generated by an electric field is proportional to the electrical energy deposition in tissue. After detecting these acoustic waves with ultrasound transducers, an image of the electric field distribution can be reconstructed in real-time. This will allow real time monitoring the IRE and provides feedback control of the treatment. Some embodiments are
(Continued)

directed to a novel EAT combined with ultrasound (EAT/US) guided IRE intervention that permits a) real time ultrasound image-guided needle placement, and b) intraoperational discrimination of IRE and RE zones during the treatment of cancer.

18 Claims, 7 Drawing Sheets

(56) References Cited

U.S. PATENT DOCUMENTS

| | | | | |
|---|---|---|---|---|
| 2013/0331699 | A1* | 12/2013 | Ishihara | G01S 15/8927 600/443 |
| 2014/0007690 | A1 | 1/2014 | Hirota | |
| 2014/0121505 | A1* | 5/2014 | Irisawa | A61B 5/0095 600/424 |
| 2019/0290903 | A1* | 9/2019 | Zarafshani | A61N 1/30 |
| 2020/0000440 | A1* | 1/2020 | Rhodes | A61B 8/585 |
| 2020/0138415 | A1* | 5/2020 | Kajiyama | G01S 15/8915 |
| 2021/0002338 | A1* | 1/2021 | Peyman | A61N 5/1028 |
| 2021/0220480 | A1* | 7/2021 | Peyman | A61P 35/04 |
| 2022/0212036 | A1* | 7/2022 | Naqa | A61B 8/08 |

OTHER PUBLICATIONS

International Search Report and Written Opinion on PCT/US2023/23896 dated Oct. 6, 2023.

* cited by examiner (a)

(b)

Figure 5(a)
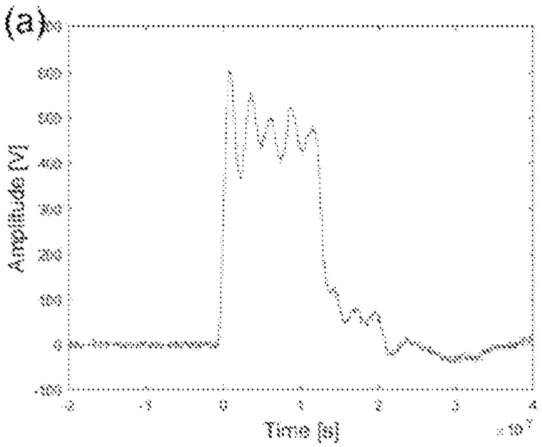
Figure 5(b)
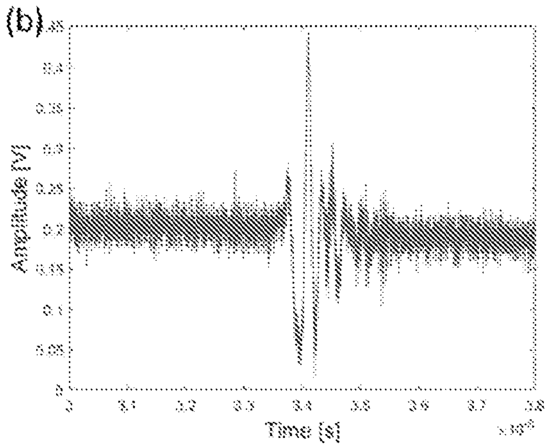
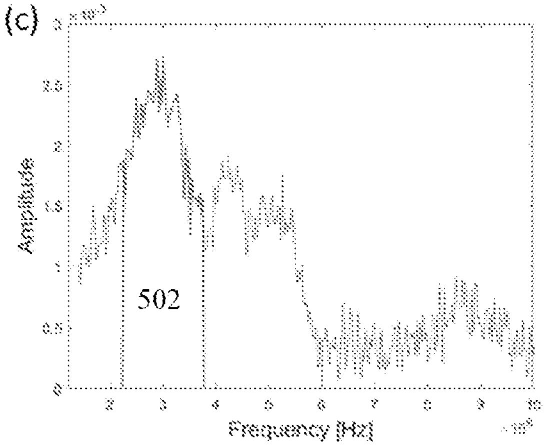
Figure 5(c)
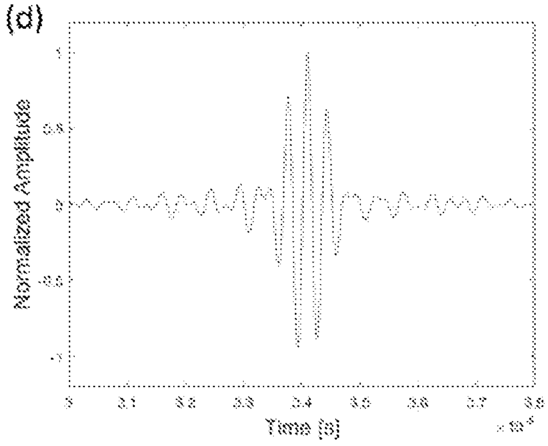
Figure 5(d)

SYSTEM AND METHOD OF DUAL-MODE EAT/US-GUIDED ELECTROPORATION

CROSS-REFERENCE TO RELATED APPLICATIONS

The present application is a National Stage Entry under 35 U.S.C. § 371 of International Application No. PCT/US2023/023896, filed May 30, 2023, which claims priority to U.S. Provisional Patent Application No. 63/347,493 filed May 31, 2022, the contents of which are incorporated herein by reference in their entirety.

TECHNICAL FIELD

The present embodiments relate generally to medical care and more particularly to a system and method for electroacoustic tomography (EAT) that can be used in EAT/US-guided electroporation.

BACKGROUND

Irreversible electroporation (IRE) is a nonthermal tissue ablation technique that causes cell death in tumor tissue while preserving the extracellular matrix and inducing minimal inflammation, which makes it a promising treatment for unresectable liver tumors. Reversible electroporation (RE) zones, incomplete tumor treatment areas, are risks of tumor recurrence and local tumor progression. Therefore, accurate prediction of RE zones can protect the effective residual liver function after the IRE ablation and guide clinicians in adopting appropriate treatment plans for patients.

It is against this technological backdrop that the present Applicant sought a technological solution to these and other problems rooted in this technology.

SUMMARY

The present embodiments relate generally to medical care and more particularly to a new imaging modality referred to herein as electroacoustic tomography (EAT) that not only depicts electrical field energy distribution in real time, but also enables clear discrimination between IRE and RE zones in situ during the treatment. According to some aspects, EAT exploits the phenomenon that the amplitude of acoustic emission generated by an electric field is proportional to the electrical energy deposition in tissue. After detecting these acoustic waves with ultrasound transducers, an image of the electric field distribution can be reconstructed in real-time. This allows real time monitoring of the IRE and provides feedback control of the treatment. Some embodiments are directed to a novel EAT combined with ultrasound (US) (EAT/US) guided IRE intervention that permits a) real time ultrasound image-guided needle placement, and b) intraoperational discrimination of IRE and RE zones during the treatment of cancer.

One object of embodiments is to improve the accuracy of electroporation therapy by visualizing the distribution of the electric field and real time tracking the electrical nodes and the movement of the tumor and other surrounding normal tissue caused by body movements. Embodiments can monitor the electric field distribution around electrodes in real time during electroporation therapy, correcting for misalignment of the electric field due to target tissue geometry and morphology, thus paving the way for the current use of electroporation therapy in the clinical field. A dual-mode EAT/US image-guided electroporation system according to embodiment has great potential for personalized cancer treatment and better outcomes.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein:

FIG. 1(*b*) is an example EAT inside-tissue electrical field reconstruction according to embodiments.

FIG. 4(*b*) is an example system setup diagram according to embodiments.

FIG. 5(*a*) is an example waveform of the pulse with a pulse width of 130 ns.

FIG. 5(*b*) is an example raw signal obtained at a voltage of 450 volts for a 130 ns pulse according to embodiments.

FIG. 5(*c*) is an example Frequency distribution of the original signal according to embodiments, the orange line shows the frequency range of the filter to be applied.

FIG. 5(*d*) is an example Filtered signal according to embodiments.

FIG. 6(*b*) is an example reconstructed image of the chicken breast phantom, with the electric field range around the electrodes shown in the figure.

FIG. 7(*b*) is an example electroacoustic signal reconstruction image.

FIG. 7(*c*) is an example ultrasound/electroacoustic dual-mode fusion image according to embodiments.

DETAILED DESCRIPTION

Figure 1A:
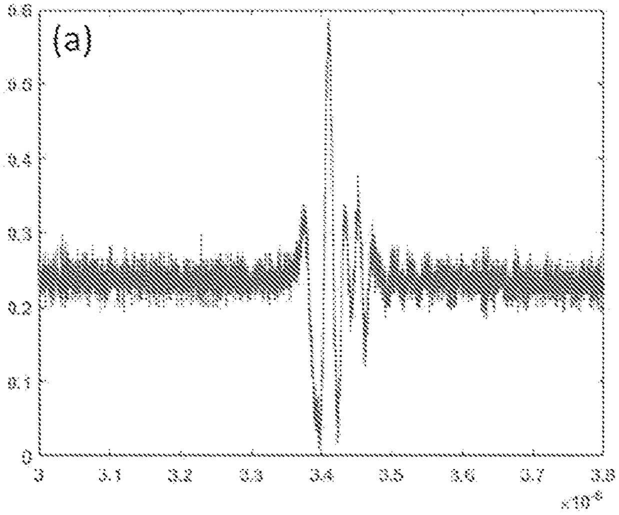
FIG. 1(*a*) is an example EAT signal according to embodiments.

The present embodiments will now be described in detail with reference to the drawings, which are provided as illustrative examples of the embodiments so as to enable those skilled in the art to practice the embodiments and alternatives apparent to those skilled in the art. Notably, the figures and examples below are not meant to limit the scope of the present embodiments to a single embodiment, but other embodiments are possible by way of interchange of some or all of the described or illustrated elements. Moreover, where certain elements of the present embodiments can be partially or fully implemented using known components, only those portions of such known components that are necessary for an understanding of the present embodiments will be described, and detailed descriptions of other portions of such known components will be omitted so as not to obscure the present embodiments. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting; rather, the present disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present embodiments encompass present and future known equivalents to the known components referred to herein by way of illustration.

As set forth above, the present embodiments are generally directed to a new imaging modality referred to herein as electroacoustic tomography (EAT) that not only depicts electrical field energy distribution in real time, but also enables clear discrimination between IRE and RE zones in situ during the treatment. EAT exploits the phenomenon that the amplitude of acoustic emission generated by an electric field is proportional to the electrical energy deposition in tissue. After detecting these acoustic waves with ultrasound transducers, an image of the electric field distribution can be reconstructed in real-time. This allows real time monitoring the IRE and provides feedback control of the treatment. Some embodiments include EAT combined with ultrasound (US) (EAT/US) guided IRE intervention that permits a) real time ultrasound image-guided needle placement, and b) intraoperational discrimination of IRE and RE zones during the treatment of cancer.

Background and Objective

Cancer is a major public health problem and the leading cause of death worldwide (Ullrich A, Miller A: Global response to the burden of cancer: the WHO approach. Am Soc Clin Oncol Educ Book2014:e311-315; Popat K, McQueen K, Feeley T W: The global burden of cancer. Best Pract Res Clin Anaesthesiol 2013, 27(4):399408). Until recently, thermal ablation techniques that relied on direct thermal effects to induce cell death have been applied for tumor ablation in clinical practice. However, many tumors cannot be treated with thermal ablation due to tumor size, hazardous tumor location, and/or the patient's poor general condition (including severe comorbidities and poor liver function). Recently emerged as a method of tumor ablation, IRE can ablate large volumes of tissue without inducing thermal effects. Importantly, IRE does not suffer from the 'heat-sink' effect, a common problem for thermal ablation methods that causes damage to adjacent parenchymal tissues and blood vessels. All these specific properties make IRE a promising treatment for patients who are not candidates for surgery and/or cannot tolerate thermal ablative techniques. Additional advantages of IRE ablation include triggering anti-tumor specific immunological reaction and having minimal impact on the tissue collagen network. These benefits make IRE an attractive approach for the treatment of patients with unresectable tumors. Developing non-invasive imaging techniques for intraoperatively accurate prediction a central of complete necrotic tissue (IRE zone) after-IRE procedures and early identification of inadequately treated reversibly electroporated tumor tissues (RE zone) will be critical for broad, effective clinical application.

Current Techniques for Detecting Electric Field Distribution in Electroporation Several methods have been proposed for monitoring electroporation therapy. For example, electrical impedance tomography (EIT) is used to detect electroporation processes, but its spatial resolution is limited (R. V. Davalos, D. M. Otten, L. M. Mir, and B. Rubinsky, "Electrical impedance tomography for imaging tissue electroporation," IEEE Trans.Biomed. Eng., vol. 51, no. 5, pp. 761-767, May 2004; Y. Granot, A. Ivorra, E. Maor, and B. Rubinsky, "In vivo imaging of irreversible electroporation by means of electrical impedance tomography," Phys. Med. Biol., vol. 54, no. 16, pp. 4927-4943, 2009). The maximum spatial resolution of EIT is lower than that of computed tomography (CT) and magnetic resonance imaging, making its application limited (T. K. Bera, "Applications of electrical impedance tomography (EIT): A short review," presented at the 3rd Int. Conf. Commun. Syst., 2018. [Online]. Available: http://iopscience.iop.org/article/10.1088/1757899X/331/1/012004/meta). Therefore, some high-resolution methods have been proposed, such as magnetic resonance EIT (MREIT) methods and impedance acoustic tomography methods (J. K. Seo and E. J. Woo, "Magnetic resonance electrical impedance tomography (MREIT)," SIAM Rev., vol. 53, no. 1, pp. 40-68, February 2011; B. Gebauer and O. Scherzer, "Impedance-acoustic tomography," SIAM J. Appl. Math., vol. 69, no. 2, pp. 565-576, December 2008.). However, MRI-based methods are costly and lack real-time performance. The use of impedance acoustic tomography to monitor the electric field distribution in real time has not yet been investigated. There are also methods such as confocal microscopy (Hemmler, R., Böse, G., Wagner, R. and Peters, R., "Nanopore unitary permeability measured by electrochemical and optical single transporter recording," Biophys. J. 88(6), 4000-4007 (2005); Vincelette, R. L., Roth, C. C., McConnell, M. P., Payne, J. A., Beier, H. T. and Ibey, B. L., "Thresholds for phosphatidylserine externalization in Chinese hamster ovarian cells following exposure to nanosecond pulsed electrical fields (nsPEF)," PloS one 8(4), e63122 (2013)). These methods are suitable for pre- and post-stimulation exposure to electric fields, but do not allow for real-time monitoring during the distribution of the electric field.

EAT as Image Guidance and Dosimeter for Electroporation Therapy

It is believed that the present Applicant's recent work represents the first study of electric field-induced acoustic tomography in the localization of electric field distributions. In 2018, the present Applicant presented the first electrical pulse-induced acoustic tomography (EAT) for electroporation treatment process monitoring (Zarafshani, A., Dang, N., Samant, P., Faiz, R., Zheng, B., & Xiang, L. Z. (2018). Real-time in-situ monitoring of electrotherapy process using Electric pulse induced Acoustic Tomography (EpAT). Medical Imaging 2018: Physics of Medical Imaging, 10573. https://doi.org/Unsp 105732j, 10.1117/12.2293138; Zarafshani, A., Merrill, J., Wang, S. Q., Zheng, B., & Xiang, L. Z. (2019). Electroacoustic tomography system with nanosecond electric pulse excitation source. Medical Imaging 2019: Ultrasonic Imaging and Tomography, 10955.https://doi.org/Unsp 109551b, 10.1117/12.2513051). And in subsequent work, electroacoustic signal acquisition and 2D image reconstruction were achieved. It was found that the electrical pulse-induced acoustic signal's correlated positively with the amplitude of the electrical pulse, which opened up the possibility of using EAT for real-time analysis in electroporation therapy.

Figure 1B:
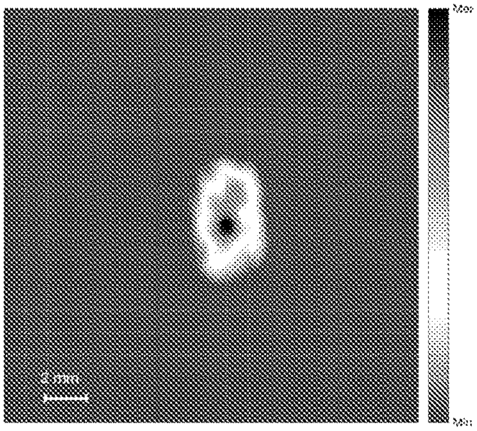

No other group has yet investigated this phenomenon. Past studies by the present Applicant have included electroacoustic signal detection, computer simulation of electroacoustic laminar imaging and two-dimensional EAT image reconstruction based on an electronically controlled rotation system (Wang, M., Zarafshani, A., Samant, P., Merrill, J., Li, D., & Xiang, L. (2020). Feasibility of Electroacoustic Tomography: A Simulation Study. IEEE Trans Ultrason Ferroelectr Freq Control, 67(5), 889-897.https://doi.org/10.1109/TUFFC.2019.2955900; Wang, S., Zarafshani, A., & Xiang, L. (2021). Electroacoustic tomography (EAT): 2D electric field reconstruction for electroporation treatment monitoring (Vol. 11598). SPIE.

https://doi.org/10.1117/12.2580691). In one of the earliest signal detection studies, researchers used a homemade nanosecond pulse generator to successfully generate clear electroacoustic signals with a pulse width of 1 microsecond and a pulse amplitude of 1.2 kV, thus verifying the feasibility of this technique. In subsequent work, the researchers also used EAT process simulations based on MATLAB partial differential equations (PDEs) and the K-Wave simulation toolbox (Id.). The results of the simulations demonstrated the distribution of the electric field around the electrodes in the tissue, and in addition it was found that both the amplitude of the electrical pulse and the spacing between the electrodes would significantly affect the distribution of the electric field. These results provided a reference for subsequent studies. Later, also scanned were the electrodes on a ring track using a single ultrasonic transducer by an electronically controlled rotation system and obtained clearer images of the electric field distribution (Id.). However, such systems often require several minutes to reconstruct the desired two-dimensional images, which makes their clinical application impossible. Therefore, in a recent study, the present Applicant successfully used a 128-element ring ultrasound transducer array to achieve real-time imaging of chicken breast tissue, obtaining reconstructed images of electric field distribution similar to those in previous studies. And a EAT/US dual-mode system to be described in more detail below was also developed, which can obtain the electric field distribution information provided by EAT and the tissue structure information provided by ultrasound in real time. FIG. 1(*a*) is an example EAT signal and FIG. 1(*b*) is an example EAT inside-tissue electrical field reconstruction according to the studies described above.

Summary of EAT

Among several aspects, the present embodiments enable the end user—the medical physicist—to monitor the electric field distribution in the tissue in real time. It is believed that electrical pulse-induced acoustic tomography (EAT) can be used for on-line electric field energy monitoring during electroporation cancer ablation therapy, thus advancing the clinical application of this non-radiological cancer treatment method. In the acoustic phenomenon induced by an electrical pulse, the electric field generated by the electrical pulse is absorbed and converted into heat; the subsequent thermoelastic expansion generates acoustic waves that can be imaged by an acoustic detector, which in turn can determine the extent of the electric field distribution. In addition, the intensity of the generated acoustic signal is linearly proportional to the intensity of the electric field; this feature allows the electroacoustic signal to monitor the energy intensity during electroporation treatment, thereby reducing the impact on healthy tissue. Adding pulsed and echo ultrasound to the EAT imaging allows the medical physicist to monitor the geometric and morphological misalignment of the electric field relative to the target tissue in real time. The present embodiments have the ability to further implement electroporation tumor ablation therapy as an effective alternative to radiotherapy.

The long-term clinical impact of these studies are profound:

- I. Ultrasound image-guided IRE monitoring techniques should permit patient-specific protocol optimization to reduce liver toxicity and improve therapy response.
- II. Intraoperatively detection of remnant, untreated tumor tissues could prompt immediate re-treatment and/or administration adjuvant therapies (RFA, radio embolization, and chemo-embolization) as needed.
- III. The development of selectively targeted IRE ablation methods should foster clinical extension of this innovative new treatment modality to other solid organ systems (renal, pancreatic, or uterine tumors).

Detailed Description of EAT

Figure 2:
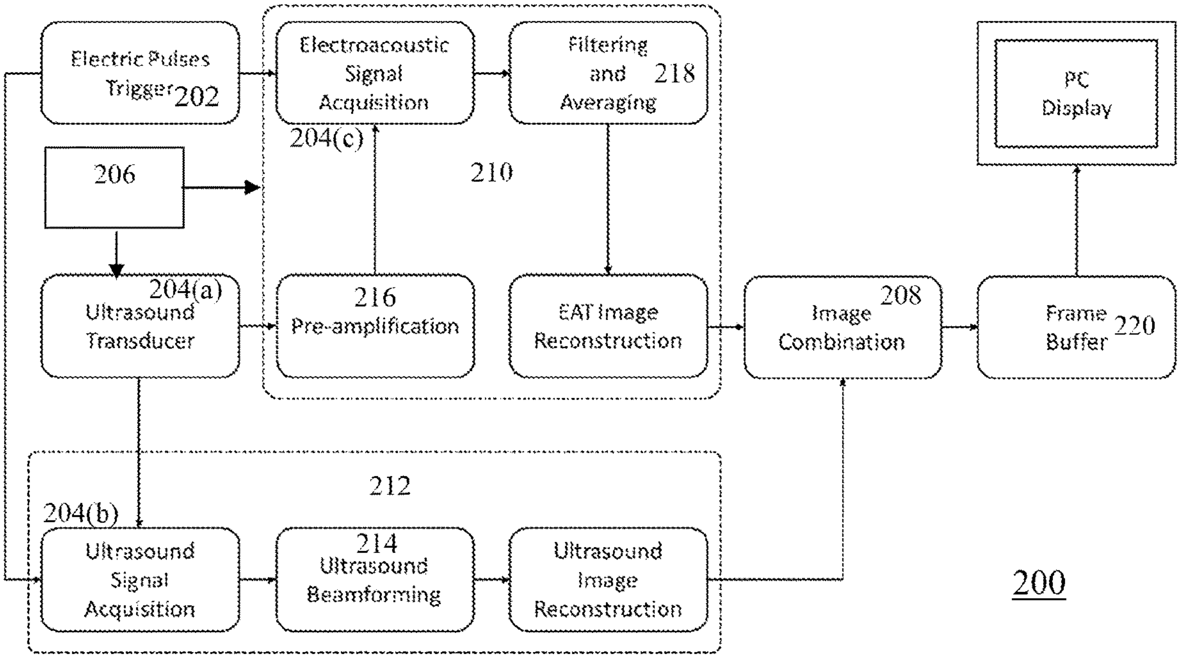
FIG. 2 is an example Combined Electroacoustic and ultrasound imaging system diagram according to embodiments.

The present disclosure provides systems and methods for generating electroacoustic images and ultrasound images in real time. An exemplary system 200 related to the present disclosure comprises the components shown in FIG. 2:

- 202: A device for generating an electrical field induced acoustic signal
- 204: A two-dimensional ultrasound array transducer adapted to (a) transmitting ultrasound waves, (b) Receive ultrasound signal reflections from transmitted ultrasound waves and (c) receiving electro-acoustic signals generated from an electrical pulse generation device
- 206: A trigger sequencing logic device for switching the connection of the ultrasound transducer between ultrasound transmission/reception and electro-acoustic signal acquisition.
- 208: An image combining device to receive and combine the results of the reconstructed EAT imaging unit 210 and the ultrasound unit 212

Those skilled in the art will understand how to implement the various components of example system 200 described above using various combinations of hardware and/or software after being taught about the associated example functionalities of these components herein, as well as by adapting techniques of the background art as described in the referenced publications.

Figure 3:
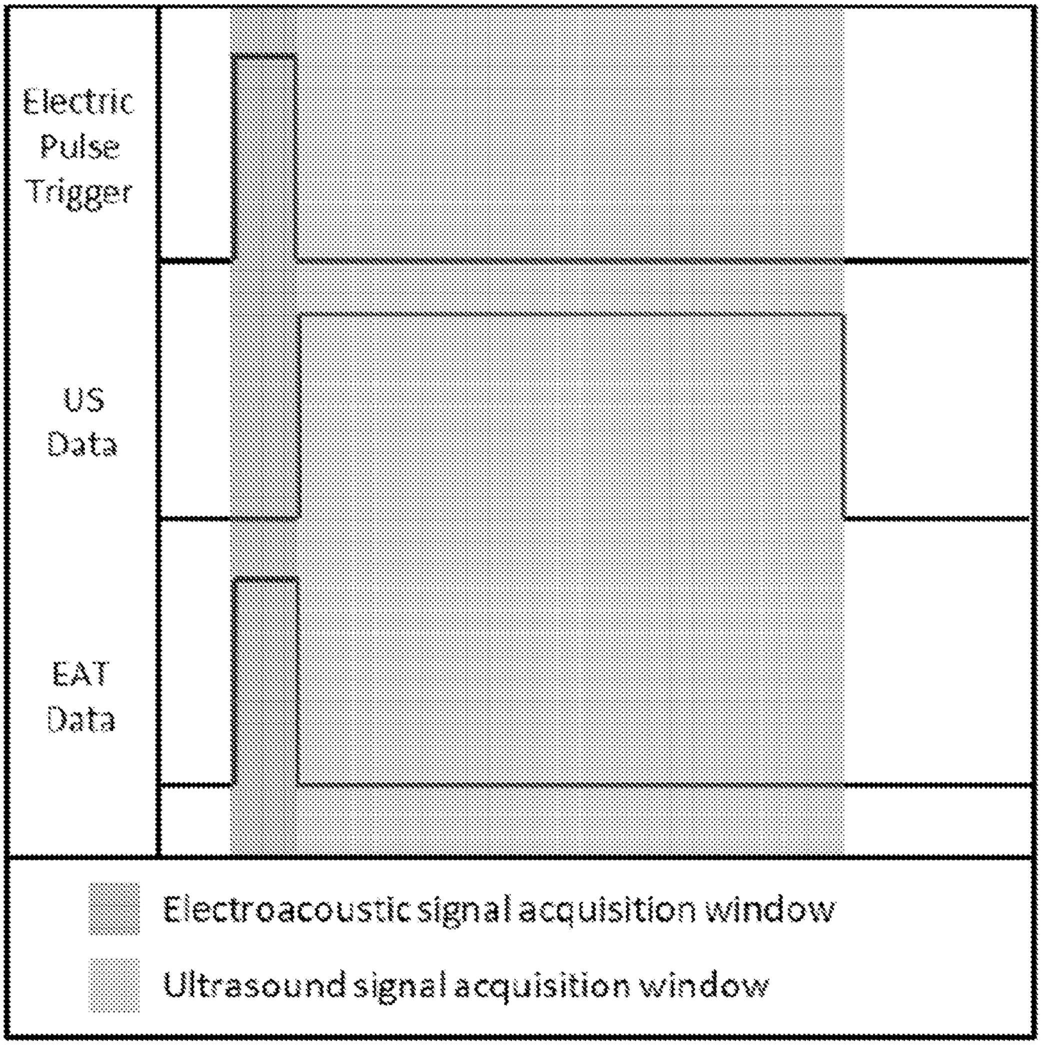
FIG. 3 is an example trigger sequencing logic demonstration according to embodiments.

In an exemplary embodiment, the ultrasound signal and the EAT signal are received in different time windows by units 212 and 210, respectively, as shown in FIG. 3.

To generate an ultrasound reconstruction image by unit 212, the transducer signals are first collected in an ultrasound reception window controlled by a flip-flop sequencing logic switch. The collected signals are beamformed by an ultrasonic beamformer 214 to produce a series of radio frequency signals. The radio frequency signals are reconstructed to produce an ultrasound image. For the EAT imaging section 210, the transducer signal is collected as soon as an electrical pulse signal trigger is detected. To compensate for the relatively small electro-acoustic signals, a multi-channel pre-amplification stage 216 is built into the first stage of the electro-acoustic imaging data acquisition and processing unit. After pre-amplification, the analogue electro-acoustic signals are acquired and converted to digital signals, followed by an averaging/filtering stage 218. After averaging and filtering, the processed signal data can be used for electro-acoustic imaging reconstruction. An image combiner 208 is used to spatially resample the averaged electroacoustic imaging reconstructions so that they can be superimposed on top of the ultrasound reconstruction image. Temporal up-sampling can also be performed on one or both modal reconstructions so that the electroacoustic frames can be interpolated for each ultrasound frame to produce a combined image frame for frame buffer 220, adapted to be displayed on a PC monitor, for example.

Example Benefits and Advantages

1. The present embodiments reconstruct the intensity distribution of the electric field in the tissue at the current moment by real-time monitoring of the ultrasound signal induced by the electric field in the tissue. It provides real-time image guidance for electroporation tumor ablation treatment and improves the accuracy of treatment.
2. The method is able to obtain electric field information in real time compared to offline pre/post-surgical electric field detection methods, reducing the effects due to breathing and other body movements.
3. The anatomical information of tissues can be obtained by ultrasound imaging, while the acquired EAT images can provide information on local tissue electric field energy deposition.
4. EAT/US imaging will provide additional information that is valuable during electroporation tumor ablation therapy, as it can greatly improve the accuracy of tumor targeting and largely mitigate adverse collateral damage to surrounding normal tissues, thus leading to better patient prognosis.

As set forth above, some embodiments are directed to Electroacoustic tomography for the guidance of electroporation.

Purpose of Electroporation

Electroporation is a clinical electrotherapy technique that uses the local application of short, strong electrical pulses to deliver drugs to the target area or to directly induce tumor cell apoptosis. Since the size, location, shape and tissue environment of the treated target varies, it is necessary to monitor the distribution of the electric field in real time. The lack of methods to directly visualize the electric field distribution has limited its clinical application. The present Applicant demonstrates for the first time the acoustic signal induced by electric fields and its potential for real-time, in situ electrotherapy monitoring.

Example Electroporation Methods

Measurement of acoustic signals induced by pulsed electric fields for real-time electrotherapy monitoring. The pulsed electric field causes a transient and localized temperature rise, which results in detectable acoustic waves in the ultrasound system due to thermoelastic expansion. This is referred to as the electroacoustic effect. Some embodiments use a nanosecond pulse generator to induce the electroacoustic signal and a single transducer and ring array of ultrasound transducers to receive the signals.

Example Conclusions

The high-resolution EAT images can be directly used for real-time monitoring electrotherapy in situ and has potential for translation in clinical applications.

Example Results

Pulsed electric field-induced acoustic waves were measured at different electric field voltages. The relationship between the electroacoustic signal strength and the applied voltage has been tested and quantified. Moreover, different concentrations of sodium chloride has been tested within agar phantoms. Finally, the electric field distribution has been imaged with EAT in real-time in chicken breast tissue.

Figure 4A:
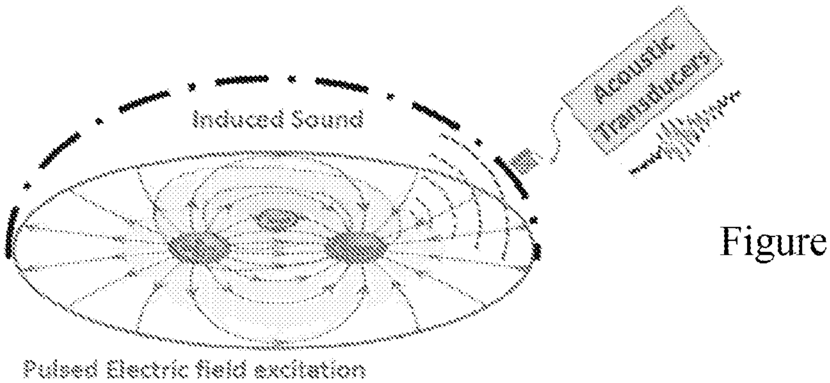
FIG. 4(*a*) is an example Schematic illustration of Electric pulse-induced Acoustic Signals according to embodiments.
Figure 4B:
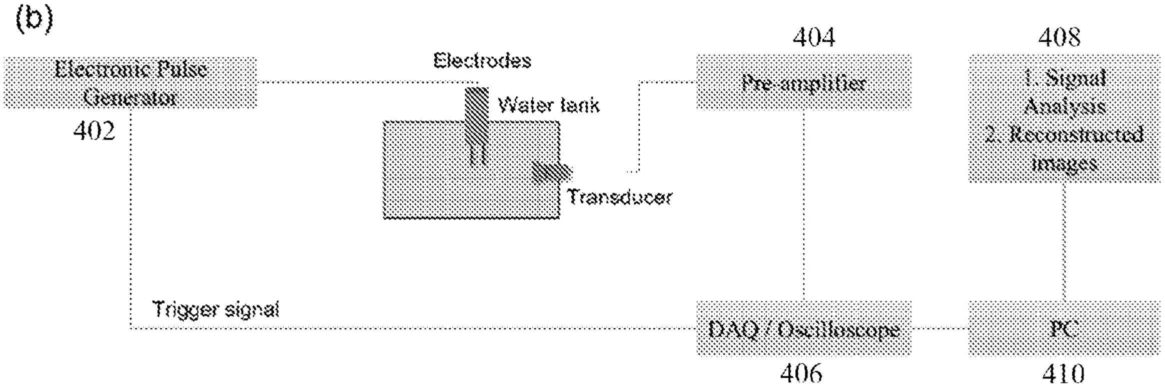

FIG. 4(*a*) is an example schematic illustration of Electric pulse-induced Acoustic Signals. In this novel technique, non-ionizing electric pulses are induced in biological tissue. The absorption of electrical energy induces a mK temperature rise, leading to transient thermoelastic expansion and wideband MHz acoustic emission. The acoustic signals are then detected by ultrasonic transducers.

FIG. 4(*b*) is an example System setup diagram. The collected signals induced by a pulse generator 402 are first amplified by a preamplifier 404, then acquired by an oscilloscope or DAQ 406, and finally sent to a PC 410 for data processing using Matlab (shown as 408).

FIG. 5(*a*) is an example Waveform of the pulse with a pulse width of 130 ns.

FIG. 5(*b*) is an example raw signal obtained at a voltage of 450 volts for a 130 ns pulse.

FIG. 5(*c*) is an example Frequency distribution of the original signal, the line 502 shows the frequency range of the filter to be applied.

FIG. 5(*d*) is an example Filtered signal.

Figure 6A:
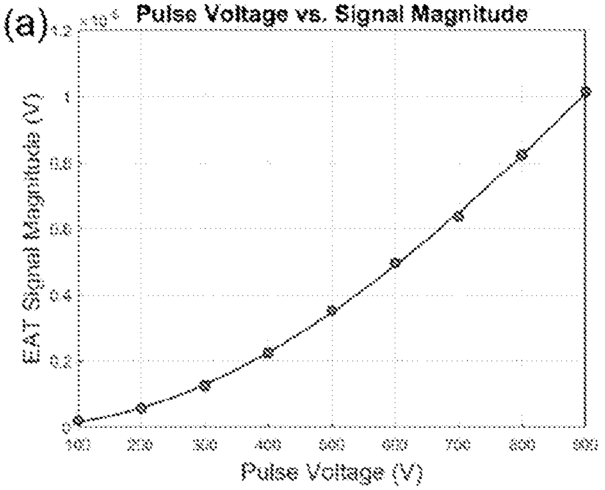
FIG. 6(*a*) illustrates an example of the amplitude of the electroacoustic signal corresponding to the voltage applied to the electrode is set from 100 to 900 volts according to embodiments.
Figure 6B:
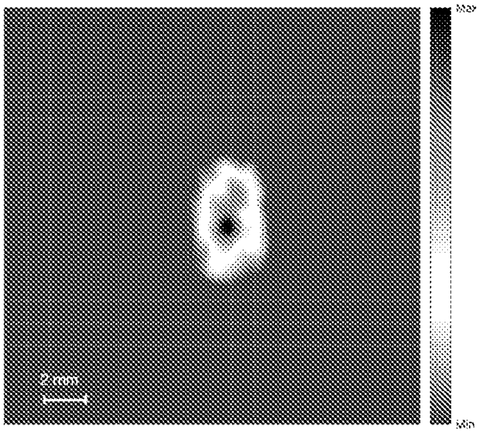

FIG. 6(*a*) is an example of the amplitude of the electroacoustic signal corresponding to the voltage applied to the electrode is set from 100 to 900 volts.

Figures 7A, 7B, 7C:
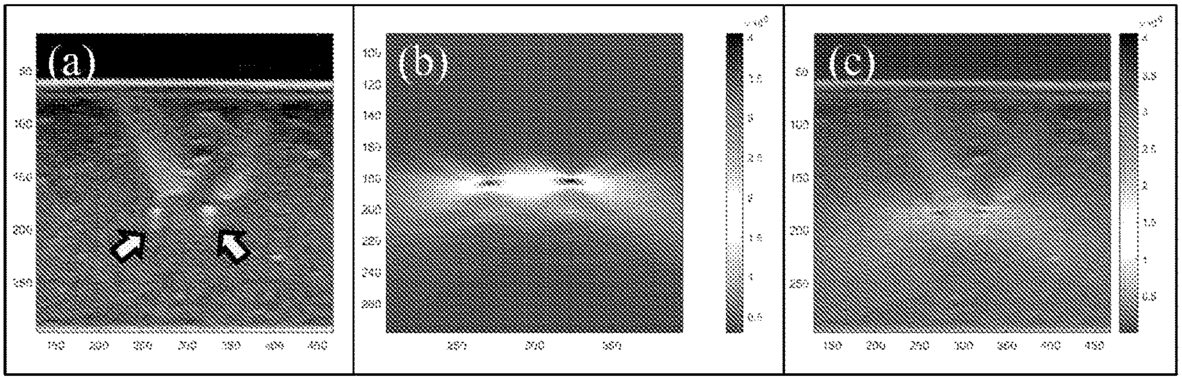
FIG. 7(*a*) is an example Ultrasound mode image with the positions of the two electrodes marked by arrows.

FIG. 6(*b*) is a reconstructed image of the chicken breast phantom, with the electric field range around the electrodes shown in the figure Additional Results A saline gel with a concentration of 1% was used as a mimic and tungsten electrodes with a spacing of 5 mm were inserted to simulate the electroporation treatment process. As shown in FIG. 7(*a*), the position of the electrode during the experiment can be monitored in ultrasound images in real time. The reconstructed EAT images are shown in FIG. 7(*b*). It can be found that the strongest signals are distributed around the electrodes and diminish with distance. A ring-shaped signal distribution appears around the electrode, which matches the theoretical distribution of the electric field. FIG. 7(*c*) illustrates an example ultrasound/electroacoustic dual-mode fusion image of FIGS. 7(*a*) and 7(*b*) according to embodiments.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

Although the present embodiments have been particularly described with reference to preferred examples thereof, it should be readily apparent to those of ordinary skill in the art that changes and modifications in the form and details may be made without departing from the spirit and scope of the present disclosure. It is intended that the appended claims encompass such changes and modifications.

What is claimed is:

1. A system for electroacoustic tomography (EAT) including:

a receiver device that is adapted to commonly receive both ultrasound signals reflected from transmitted ultrasound waves and also to receive electroacoustic signals generated from an electrical pulse generation device;

an EAT imaging unit adapted to generate an electroacoustic image based on the received electroacoustic signals, including a preamplification stage to amplify the electroacoustic signals relative to the ultrasound signals that are commonly received by the receiver device;

an ultrasound imaging unit adapted to generate an ultrasound image based on the received ultrasound signals; and an image combining device adapted to receive and combine the generated electroacoustic image and ultrasound image.

2. The system of claim 1, further comprising:

an electroacoustic device adapted to generate an electrical field induced acoustic signal; and an ultrasound device adapted to transmit ultrasound waves.

3. The system of claim 1, wherein the receiver device is comprised of an ultrasound transducer, the system further comprising a trigger sequencing logic device for switching a connection of the ultrasound transducer between ultrasound transmission/reception and electroacoustic signal acquisition.

4. The system of claim 3, wherein the trigger sequencing logic device is configured to perform switching such that the ultrasound signal and the electroacoustic signal are received in different time windows.

5. The system of claim 1, wherein the ultrasound imaging unit includes:

a transducer adapted to receive ultrasound signals in an ultrasound reception window controlled by a flip-flop sequencing logic switch;

an ultrasonic beamformer adapted to produce a series of radio frequency signals from the ultrasonic signals; and an ultrasound image construction unit adapted to produce the ultrasound image from the radio frequency signals.

6. The system of claim 1, wherein the EAT imaging unit further includes:

an acquisition stage adapted to collect an electroacoustic signal in response to an electrical pulse signal trigger;

an averaging/filtering stage adapted to process an amplified electroacoustic signal from the pre-amplification stage; and an EAT image construction unit adapted to perform electroacoustic imaging reconstruction.

7. The system of claim 1, wherein the image combiner uses spatial resampling to produce averaged electroacoustic imaging reconstructions so that the electroacoustic image can be superimposed on top of the ultrasound image.

8. The system of claim 7, wherein the image combiner produces combined image frames for display.

9. A method for electroacoustic tomography (EAT) including:

commonly receiving, via a receiver device, both ultrasound signals reflected from transmitted ultrasound waves and electroacoustic signals generated from an electrical pulse generation device;

amplifying the electroacoustic signals relative to the ultrasound signals that are commonly received by the receiver device;

generating, by an EAT imaging unit, an electroacoustic image based on the received electro-acoustic signals after amplification;

generating, by an ultrasound imaging unit, an ultrasound image based on the received ultrasound signals; and receiving, by an image combining device, the generated electroacoustic image and ultrasound image and combining them to generate a combined image.

10. A method according to claim 9, further comprising:

depicting electrical field energy distribution in real time;

enabling clear discrimination between irreversible electroporation (IRE) zones and reversible electroporation (RE) zones in situ during treatment, including exploiting the phenomenon that the amplitude of acoustic waves generated by an electric field is proportional to the electrical energy deposition in tissue; and after detecting the acoustic waves with ultrasound transducers, constructing an image of the electric field distribution in real-time.

11. The method of claim 10, further comprising enabling real time ultrasound image-guided needle placement.

12. The method of claim 9, further comprising:

generating an electrical field induced acoustic signal; and transmitting ultrasound waves.

13. The method of claim 9, further comprising switching a connection of an ultrasound transducer between ultrasound transmission/reception and electroacoustic signal acquisition.

14. The method of claim 13, wherein switching includes performing the switching such that the ultrasound signal and the electroacoustic signal are received in different time windows.

15. The method of claim 9, wherein generating the ultrasound image includes:

receiving ultrasound signals in an ultrasound reception window controlled by a flip-flop sequencing logic switch;

producing a series of radio frequency signals from the ultrasonic signals; and producing the ultrasound image from the radio frequency signals.

16. The method of claim 9, wherein generating the electroacoustic image includes:

collecting an electroacoustic signal in response to an electrical pulse signal trigger;

processing the electroacoustic signals that have been amplified relative to the ultrasound signals in an averaging/filtering stage; and performing electroacoustic imaging reconstruction based on the processed electroacoustic signals.

17. The method of claim 9, wherein combining includes using spatially resampling to produce averaged electroacoustic imaging reconstructions so that the electroacoustic image can be superimposed on top of the ultrasound image.

18. The method of claim 17, further including producing combined image frames for display.

* * * * *